United States Patent
Boutros et al.

(10) Patent No.: US 9,877,484 B2
(45) Date of Patent: Jan. 30, 2018

(54) PULVURENT EFFERVESCENT TOPICAL TREATMENT COMPOSITION

(71) Applicant: Reckitt Benckiser LLC, Parsippany, NJ (US)

(72) Inventors: Iriny Boutros, Montvale, NJ (US); Sarah Frances De Szalay, Montvale, NJ (US)

(73) Assignee: RECKITT BENCKISER LLC, Parsippany, NJ (US)

( * ) Notice: Subject to any disclaimer, the term of this patent is extended or adjusted under 35 U.S.C. 154(b) by 0 days.

(21) Appl. No.: 15/115,403

(22) PCT Filed: Feb. 13, 2015

(86) PCT No.: PCT/GB2015/050399
§ 371 (c)(1),
(2) Date: Jul. 29, 2016

(87) PCT Pub. No.: WO2015/121659
PCT Pub. Date: Aug. 20, 2015

(65) Prior Publication Data
US 2017/0006874 A1    Jan. 12, 2017

Related U.S. Application Data

(60) Provisional application No. 61/940,050, filed on Feb. 14, 2014.

(30) Foreign Application Priority Data

Feb. 10, 2015  (GB) .................................. 1502144.7

(51) Int. Cl.
| | | |
|---|---|---|
| *A01N 59/04* | (2006.01) | |
| *A61K 8/73* | (2006.01) | |
| *A61Q 19/10* | (2006.01) | |
| *A61K 8/02* | (2006.01) | |
| *A01N 37/40* | (2006.01) | |
| *A61K 8/22* | (2006.01) | |
| *A61K 8/97* | (2017.01) | |

(52) U.S. Cl.
CPC ............ *A01N 59/04* (2013.01); *A01N 37/40* (2013.01); *A61K 8/022* (2013.01); *A61K 8/22* (2013.01); *A61K 8/73* (2013.01); *A61K 8/975* (2013.01); *A61Q 19/10* (2013.01); *A61K 2800/222* (2013.01)

(58) Field of Classification Search
CPC ........ A01N 37/40; A01N 59/04; A01N 37/36; A01N 63/04; A61K 2800/222; A61K 8/022; A61K 8/22; A61K 8/73; A61K 8/975; A61Q 19/10

See application file for complete search history.

(56) References Cited

U.S. PATENT DOCUMENTS

| | | | | |
|---|---|---|---|---|
| 4,971,786 A | * | 11/1990 | Grollier ................. | A61K 8/416 424/47 |
| 5,912,002 A | * | 6/1999 | Grieveson .............. | A61K 8/066 424/401 |
| 6,723,330 B2 | * | 4/2004 | Bergquist ................ | A61K 8/02 424/400 |
| 2014/0199351 A1 | * | 7/2014 | McCoy ................ | A61K 8/0216 424/401 |

FOREIGN PATENT DOCUMENTS

| | | |
|---|---|---|
| DE | 4224714 A1 | 2/1994 |
| DE | 10338615 A1 | 3/2005 |
| EP | 0987010 A2 | 3/2000 |
| WO | 9617922 A1 | 6/1996 |

OTHER PUBLICATIONS

International Search Report for corresponding application PCT/GB2015/050399 dated May 12, 2015.
Written Opinion of the International Searching Authority for corresponding application PCT/GB2015/050399 dated May 12, 2015.

* cited by examiner

*Primary Examiner* — Ernst V Arnold
(74) *Attorney, Agent, or Firm* — Norris McLaughlin & Marcus PA

(57) ABSTRACT

The pulvurent effervescent topical treatment compositions comprise:
  at least 50% wt. of a gas generating system which comprises both a gas generating constituent as well as a complementary reactive acid constituent, which constituents, when combined in the presence of water or another largely aqueous medium generates a gas, preferably carbon dioxide;
  5-50% wt. of an anionic soap and/or anionic surfactant constituent;
  0.0001-1.5% wt. of an antimicrobial constituent;
  0.0001-3 an exogenous product of *Sclerotium rolfsii*,
  and, optionally one or more filler constituents, preferably based on materials which are inert with respect to the gas generating constituent and which also are inert with respect to the antimicrobial constituent;
  further optionally, one or more further constituents which may be included to provide a desired aesthetic benefit, e.g., a fragrance, colorant and/or a desired technical benefit, e.g. an abrasive, to the pulvurent effervescent topical treatment compositions of which they form a part.
The invention also provides effervescing, foamed topical treatment composition which are used as topical treatment compositions.

17 Claims, No Drawings

PULVURENT EFFERVESCENT TOPICAL TREATMENT COMPOSITION

This is an application filed under 35 USC 371 of PCT/GB2015/050399, which in turn claims the priority benefit of U.S. Ser. No. 61/940,050 filed 14 Feb. 2014, and UK 1502144.7 filed 10 Feb. 2015, and the benefit of all priority claims is hereby made. Further, the entirety of the disclosures of the foregoing documents is herein fully incorporated by reference.

The present invention relates to a pulvurent effervescent topical treatment composition which, when contacted with an aqueous medium, exhibits a foaming effect and which additionally provides an antimicrobial benefit to treated topical surfaces.

Topical compositions, per se, are well-known in the cosmetic, dermatological as well as in the pharmaceutical fields. Most topical compositions are intended to provide at least one but generally provide multiple or more specific benefits after being applied to the human skin. For example, personal care compositions which are primarily intended to be soaps for general cleaning of the human skin such as hand soaps or body wash soaps are well known in the fields of cosmetics and personal care products. While providing a primary cleaning benefit, such personal care compositions frequently also provide ancillary benefits such as moisturizing and nourishing the skin. Such personal care compositions which provide a good general cleaning benefit are usually based on one or more anionic soaps or anionic surfactants which are recognized to provide good cleaning and good foaming. However, such foaming compositions are most frequently provides a liquids which are dispensed through a specialized dispensing pump or nozzle which induces air entrainment in the liquid and hence such appear as a foam when topically applied. While advantageous, such foaming compositions require both that the composition be any flowable, liquid form and that the specialized dispensing pump nozzle be used.

While the prior art includes such topical compositions for use in handwash and bodywash applications, there is nonetheless a real and continuing need in the art for further improvements to such compositions. It is to these and further shortcomings in the art to which the present inventive compositions and methods for their use are directed.

In a first aspect of the present invention there is provided a pulvurent effervescent topical treatment composition which, when contacted with an aqueous medium, exhibits a foaming effect and which additionally provides an antimicrobial benefit to treated topical surfaces.

In a second aspect, the present invention provides a method for the manufacture or production of pulvurent effervescent topical treatment compositions as set forth herein.

In a third aspect of the invention, there is provided an aqueous topical treatment compositions, which compositions exhibit a foaming effect and provide an antimicrobial effect, which compositions are formed from the addition of water to the pulvurent effervescent topical treatment compositions as set forth herein.

In a fourth aspect the present invention provides a method for providing an antimicrobial benefit to a topical surface, e.g., the epidermis or other body area or hair, which method includes the step of applying an antimicrobially effective amount of a topical germicidal composition as taught herein, preferably to reduce the incidence of undesired microorganisms present on the treated topical surface, other body surface or hair.

According to a fifth aspect, the present invention provides a topical germicidal composition according to the any of the prior aspects of the invention, characterized in that the said composition is effective against one or more, preferably at least two or more of, still more preferably at least three or more of the following microorganisms: *E. coli, S. aureus, P. aeruginosa*, and *E. hirae*.

These and further aspects of the invention will become more apparent from a reading of the following specification.

The pulvurent effervescent topical treatment compositions comprise:
- at least 50% wt. of a gas generating system which comprises both a gas generating constituent as well as a complementary reactive acid constituent, which constituents, when combined in the presence of water or another largely aqueous medium generates a gas, preferably carbon dioxide;
- 5-50% wt. of an anionic soap and/or anionic surfactant constituent;
- 0.0001-1.5% wt. of an antimicrobial constituent;
- 0.0001-3 an exogenous product of *Sclerotium rolfsii*,
- and, optionally one or more filler constituents, preferably based on materials which are inert with respect to the gas generating constituent and which also are inert with respect to the antimicrobial constituent;
- further optionally, one or more further constituents which may be included to provide a desired aesthetic benefit, e.g., a fragrance, colorant and/or a desired technical benefit, e.g. an abrasive, to the pulvurent effervescent topical treatment compositions of which they form a part.

The recited essential constituents of the pulvurent effervescent topical treatment compositions are most preferably in the form of generally dry, free flowing powers or in the case of any liquid constituent, have been absorbed and/or absorbed onto one or more further constituent(s) present in the pulvurent effervescent topical treatment compositions. Preferably however, each of the constituents of the gas generating system, the soap and/or surfactant constituent and the antimicrobial constituent are themselves generally free flowing powder compositions at room temperature (20-22 deg. C.) when each of these individual compositions are at a relative humidity of about 20% or less.

The pulvurent effervescent topical treatment compositions are themselves generally free flowing powder compositions at room temperature (20-22 deg. C.) when the compositions are at a relative humidity of about 20% or less. The pulvurent effervescent topical treatment compositions are readily combinable, e.g, dispersible, dissolvable, with water or with a largely aqueous medium, e.g. a aqueous/alcoholic liquid, which are used to form an aqueous topical treatment compositions, which compositions exhibit a foaming effect and provide an antimicrobial effect. Preferably the overall moisture content of the pulvurent effervescent topical treatment compositions at room temperature are about 1% wt, or less, preferably 0.5% wt, still more preferably 0.25% wt. or less of water, and most preferably the pulvurent effervescent topical treatment compositions are essentially anhydrous at these conditions.

The gas generating system comprises a gas generating constituent which generates $CO_2$ gas in the presence of the complementary reactive acid also present in the composition. In the presence of an aqueous medium, e.g. water applied to the composition, the reaction of the gas generating constituent causes the evolution of bubbles of gas from a liquid as the result of a chemical reaction, and the gas generating constituent, to produce carbon dioxide gas which in turn contributes to the foaming of the treatment compositions. Such a gas generating constituent may be interchangeably referred to as a $CO_2$ donor constituent. Known art materials can be used as the gas generating constituent including one or more materials selected from the group consisting of: carbonates, bicarbonates, sesquicarbonates, and mixtures thereof, preferably as alkali metal containing compounds. Non-limiting examples of suitable bases include sodium carbonate, potassium carbonate, magnesium carbonate, calcium carbonate, ammonium carbonate, sodium bicarbonate, potassium bicarbonate, magnesium bicarbonate, calcium bicarbonate, ammonium bicarbonate, sodium sesquicarbonate, potassium sesquicarbonate, magnesium sesquicarbonate, calcium sesquicarbonate, ammonium sesquicarbonate, and mixtures thereof. Preferably, the gas generating constituent is selected from sodium carbonate, sodium bicarbonate and mixtures thereof. Sodium bicarbonate is particularly preferred. A representative reaction is as follows:

$$NaHCO_3/Na_2CO_3 + H+ \rightarrow CO_2$$

As can be seen from the foregoing, the gas generating constituent reacts with the complementary reactive acid to form carbon dioxide gas when gas generating constituent is contacted with water, or is dispersed in water or other largely aqueous medium. The evolution of carbon dioxide gas is advantageous in the formation of the foam, and eliminates the need for any specialized pump or nozzle apparatus to provide a foaming benefit. Furthermore as the composition is pulvurent, it provide a high concentration of both the cleaning and antimicrobial constituents per unit mass of the pulvurent composition, particularly as compared to prior art liquid compositions which provide a foaming and antimicrobial benefit to topical surfaces.

Advantageously the gas generating system comprises at least 65% wt of the total weight (based on a total of 100% wt.) of the pulvurent effervescent topical treatment compositions. Preferably the gas generating system comprises between about 65% wt.-95% wt., more preferably between about 75% wt.-90% wt., and particularly preferably about 80% wt.-88% wt. of the said composition.

The gas generating constituent comprises at least 50% wt. of the total weight of the pulvurent effervescent topical treatment compositions. Preferably the gas generating constituent comprises 50% wt.-75% wt., more preferably 50% wt.-65% wt., and most preferably 50% wt.-60% wt. of the said pulvurent effervescent topical treatment compositions.

The gas generating system further comprises a complementary reactive acid. Such may be any acid, e.g, one or more inorganic acids, and/or one or more organic acids, which are water soluble or dispersible and which are also reactive with the gas generating constituent (viz., CO2 donor constituent) when combined in the presence of water. The complementary reactive acid may be one or more of a water soluble inorganic acids, mineral acids, or organic acids, with virtually all such known materials contemplated as being useful in the present inventive compositions. By way of non-limiting example useful inorganic acids include hydrochloric acid, phosphoric acid, sulfuric acid. With respect to water soluble organic acids, generally include at least one carbon atom, and include at least one carboxyl group (—COOH) in its structure. Preferred are water soluble organic acids which contain from 1 to about 6 carbon atoms, and at least one carboxyl group as noted. Preferred as the complementary reactive acid constituent are one or more organic acids selected from the group consisting of: citric acid, sorbic acid, acetic acid, boric acid, formic acid, maleic acid, adipic acid, lactic acid, malic acid, malonic acid, glycolic acid, and mixtures thereof. Each of these acids are water soluble, and comprises as least one carboxyl group (—COOH) in its structure. Desirably the complementary reactive constituent comprises citric acid and optionally one or more further of the recited organic acids, and in certain particularly preferred embodiments the complementary reactive acid constituent consists essentially of, preferably consists solely of citric acid. Particularly preferably, the complementary reactive acid is provided in a sufficient stoichiometric excess with respect to the gas generating constituent such that the remaining citric acid not consumed in the $CO_2$ generation reaction acts to adjust and/or buffer the pH of the aqueous topical treatment composition to a desired target pH.

The complementary reactive acid is present in a sufficient amount to at least react with a part of the gas generating constituent such that a gas is generated when the pulvurent effervescent topical treatment composition is combined with, contacted by, admixed in, or dissolved in a quantity of water. Desirably however the complementary reactive acid is present in a sufficient stoichiometric amount which is at least equal to the stoichiometric amount of the gas generating constituent, but preferably is present in a modest excess thereof so that a remaining amount of the complementary reactive acid imparts a pH adjusting and/or pH buffering effect described previously. However, it is at the same time desirous that the gas generating constituent is not present in excess. With this being noted, the stoichiometric ratio (molar ratio) of the complementary reactive acid:gas generating constituent is preferably such that the amount of the gas generating constituent is in an excess required for the reaction, but is within 200%, preferably within 150%, of the required molar ratio of the reaction.

In the case of the particularly preferred constituents of the gas generating constituent (sodium bicarbonate, citric acid) the gas generating reaction is as follows:

$$H_3C_6H_5O_7(aq) + 3NaHCO_3(aq) \rightarrow Na_3C_6H_5O_7(aq) + 3CO_2(g) + 3H_2O(l)$$

As is seen from the foregoing reaction equation, the required stoichiometric ratio required for complete reaction of one mol of citric acid requires 3 mols, thus according to the preferred stoichiometric ratio (molar ratio) of the complementary reactive acid:gas generating constituent, for each 1 mol of citric acid present, the required molar ratio would be 3 mols of sodium bicarbonate. Thus, in view of this required molar ratio for these specific constituents, a 200% amount would be 6 mols of sodium bicarbonate, a 150% amount would be 4.5 mols of sodium bicarbonate.

While demonstrated with the particularly preferred constituents of the gas generating constituent, it is understood that a similar calculation may be undertaken with different constituents, in order to determine the required stoichiometric ratio for such other constituents.

Alternatively the complementary reactive acid is forms at least 3% wt., preferably forms 3% wt.-40% wt., more preferably forms 10% wt.-35% wt. of the total weight of the pulvurent effervescent topical treatment compositions.

The pH of the aqueous topical treatment compositions formed from the pulvurent effervescent topical treatment compositions when combined with water or largely aqueous medium is preferably acidic. The pH of such aqueous topical treatment compositions are evaluated by forming a 10% concentration of the pulvurent effervescent topical treatment compositions in water, preferably deionized water at room temperature. In preferred embodiments the pH of such aqueous topical treatment compositions is not in excess of 7, but preferably is in the range of about 4-6.

Aqueous topical treatment compositions are formed by combining water or a largely aqueous medium with the pulvurent effervescent topical treatment compositions such that the combination causes the generation of $CO_2$ gas by the gas generating constituent, and the generation of a foam. While water may be added in any amount, preferably however the concentration of the pulvurent effervescent topical treatment compositions in water is in the range of from about 0.01%-35%, preferably in the range of about 0.5%-20% wt., and especially preferably from about 0.5%-15%, on a w/w basis.

The pulvurent effervescent topical treatment compositions necessarily comprise 5-50% wt. of an anionic soap and/or anionic surfactant constituent. Non-limiting examples of useful anionic surfactants include may be water soluble anionic sulfonate surfactants and include, but are not limited to: linear $C_8$-$C_{24}$ alkyl benzene sulfonates; $C_8$-$C_{24}$ paraffin sulfonates, alpha olefin sulfonates containing about 8 to about 24 carbon atoms and $C_8$-$C_{24}$ alkyl sulfates and mixtures thereof. These anionic surfactants may be present as water soluble or water dispersible salts, e.g., alkali metal or alkaline earth metal salts, such as sodium, potassium, ammonium, lithium magnesium as well as alkanolammonium salts of any of these aforementioned compounds.

The anionic surfactant may be any of the anionic surfactants known or previously used in the art of aqueous surfactant compositions. Suitable anionic surfactants include, but are not limited to: alkyl sulfates, alkyl ether sulfates, alkaryl sulfonates, alkyl succinates, alkyl sulfosuccinates, N-alkoyl sarcosinates, alkyl phosphates, alkyl ether phosphates, alkyl ether carboxylates, alkylamino acids, alkyl peptides, alkoyl taurates, carboxylic acids, acyl and alkyl glutamates, alkyl isethionates, and alpha-olefin sulfonates, especially their sodium, potassium, magnesium, ammonium and mono-, di- and triethanolamine salts. The alkyl groups generally contain about 8 to about 24 carbon atoms and may be unsaturated. These anionic surfactants may be provided as salts of one of these aforementioned compounds, which salts may render them, or improve their solubility or miscibility in water. Non-limiting examples of water soluble or water dispersible salts include alkali metal or alkaline earth metal salts, such as sodium, potassium, ammonium, lithium magnesium as well as alkanolammonium salts.

In certain preferred embodiments, the anionic surfactant(s) predominantly consist of one or more alkyl alkoxylated ether sulfates, e.g., alkyl ethoxylated ether sulfates or salt form thereof. Such compounds include those which may be represented by either of the following formula I and II as follows:

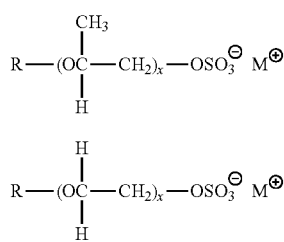

in which formulae, x has a value of from 1-22 inclusive, but preferably has a value of 1-10 inclusive, R is an alkyl group having 8-18 carbon atoms, and M is a radical or cation which renders the compound water soluble or water miscible, e.g., These anionic surfactants may be provided as salts of one of these aforementioned compounds, which salts may render them, or improve their solubility or miscibility in water. Non-limiting examples of water soluble or water dispersible salts include alkali metal or alkaline earth metal salts, such as sodium, potassium, ammonium, lithium magnesium as well as alkanolammonium salts.

An exemplary and preferred anionic surfactant is a sodium cocosulfate, which is a solid material at room temperature and which may be comminuted into a pulvurent form. Such a material is presently commercially available as Mackol® CAS-100N (ex. Rhodia).

In place or, or in addition to the recited anionic surfactants, the compositions may include an anionic soap. Such are typically anionic materials (i.e. alkali metal salts, e.g., sodium or potassium salts) of fatty acids, typically having from about 8 to about 24 carbon atoms, preferably from about 10 to about 20 carbon atoms. Further suitable soaps include alkali metal, ammonium and alkanolammonium salts of aliphatic alkane or alkene monocarboxylic acids having about 8 to about 18 carbon atoms. Sodium, potassium, ammonium, mono-, di-, and triethanolammonium cations or combinations thereof, are preferred. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps may be prepared by either direct saponification of fats and oils or by neutralization of free fatty acids. Particularly useful are the sodium, potassium, ammonium and alkanolammonium salts of lauric acid, myristic acid, palmitic acid, stearic acid, oleic acid, linoleic acid, ricinoleic acid, coconut fatty acid, palm kernel fatty acid and tallow fatty acid, as well as technical grade mixtures thereof.

Advantageously the soap and/or surfactant constituent comprises 1-40% wt., preferably about 15-30 wt., of the pulvurent effervescent topical treatment compositions. The identity of preferred anionic surfactants and/or anionic soaps, and the preferred weights thereof are described with reference to one or more of the following examples.

The pulvurent effervescent topical treatment compositions also necessarily include 0.0001-1.5% wt. of an antimicrobial constituent.

Non-limiting examples of antimicrobial constituents include: benzoyl peroxide, pyrithiones (especially zinc pyrithione which is also known as ZPT), dimethyldimethylol hydantoin (Glydant), methylchloroisothiazolinone/methylisothiazolinone (Kathon CG), sodium sulfite, sodium bisulfite, imidazolidinyl urea (Germall 115), diazolidinyl urea (Germaill II), benzyl alcohol, 2-bromo-2-nitropropane-1,3-diol (Bronopol), formalin (formaldehyde), iodopropenyl butylcarbamate (Polyphase P100), chloroacetamide, methanamine, methyldibromonitrile glutaronitrile (1,2-Dibromo-2,4-dicyanobutane or Tektamer), glutaraldehyde, 5-bromo-5-nitro-1,3-dioxane (Bronidox), phenethyl alcohol, o-phenylphenol/sodium o-phenylphenol, sodium hydroxymethylglycinate (Suttocide A), polymethoxy bicyclic oxazolidine (Nuosept C), dimethoxane, thimersal dichlorobenzyl alcohol, captan, chlorphenenesin, dichlorophene, chlorbutanol, glyceryl laurate, halogenated diphenyl ethers like 2,4,4-trichloro-2-hydroxy-diphenyl ether (Triclosan or TCS), 2,2-dihydroxy-5,5-dibromo-diphenyl ether, phenolic compounds like phenol, 2-methyl phenol, 3-methyl phenol, 4-methyl phenol, 4-ethyl phenol, 2,4-dimethyl phenol, 2,5-dimethyl phenol, 3,4-dimethyl phenol, 2,6-dimethyl phenol, 4-n-propyl phenol, 4-n-butyl phenol, 4-n-amyl phenol, 4-tert-amyl phenol, 4-n-hexyl phenol, 4-n-heptyl phenol, mono- and poly-alkyl and aromatic halophenols such as p-chlorophenol, methyl p-chlorophenol, ethyl p-chlorophenol, n-propyl p-chlorophenol, n-butyl p-chlorophenol, n-amyl p-chlorophenol, sec-amyl p-chlorophenol, n-hexyl p-chlorophenol, cyclohexyl p-chlorophenol, n-heptyl p-chlorophenol, n-octyl p-chlorophenol, o-chlorophenol, methyl o-chlorophenol, ethyl o-chlorophenol, n-propyl o-chlorophenol, n-butyl o-chlorophenol, n-amyl o-chlorophenol, tert-amyl o-chlorophenol, n-hexyl o-chlorophenol, n-heptyl o-chlorophenol, o-benzyl p-chlorophenol, o-benzyl-m-methyl p-chlorophenol, o-benzyl-m, m-dimethyl p-chlorophenol, o-phenylethyl p-chlorophenol, o-phenylethyl-m-methyl p-chlorophenol, 3-methyl p-chlorophenol, 3,5-dimethyl p-chlorophenol, 6-ethyl-3-methyl p-chlorophenol, 6-n-propyl-3-methyl p-chlorophenol, 6-iso-propyl-3-methyl p-chlorophenol, 2-ethyl-3,5-dimethyl p-chlorophenol, 6-sec-butyl-3-methyl p-chlorophenol, 2-iso-propyl-3,5-dimethyl p-chlorophenol, 6-diethylmethyl-3-methyl p-chlorophenol, 6-iso-propyl-2-ethyl-3-methyl p-chlorophenol, 2-sec-amyl-3,5-dimethyl p-chlorophenol 2-diethylmethyl-3,5-dimethyl p-chlorophenol, 6-sec-octyl-3-methyl p-chlorophenol, p-chloro-m-cresol, p-bromophenol, methyl p-bromophenol, ethyl p-bromophenol, n-propyl p-bromophenol, n-butyl p-bromophenol, n-amyl p-bromophenol, sec-amyl p-bromophenol, n-hexyl p-bromophenol, cyclohexyl p-bromophenol, o-bromophenol, tert-amyl o-bromophenol, n-hexyl o-bromophenol, n-propyl-m,m-dimethyl o-bromophenol, 2-phenyl phenol, 4-chloro-2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, para-chloro-meta-xylenol, dichloro meta xylenol, chlorothymol, 5-chloro-2-hydroxydiphenylmethane, resorcinol and its derivatives including methyl resorcinol, ethyl resorcinol, n-propyl resorcinol, n-butyl resorcinol, n-amyl resorcinol, n-hexyl resorcinol, n-heptyl resorcinol, n-octyl resorcinol, n-nonyl resorcinol, phenyl resorcinol, benzyl resorcinol, phenylethyl resorcinol, phenylpropyl resorcinol, p-chlorobenzyl resorcinol, 5-chloro 2,4-dihydroxydiphenyl methane, 4-chloro 2,4-dihydroxydiphenyl methane, 5-bromo 2,4-dihydroxydiphenyl methane, and 4-bromo 2,4-dihydroxydiphenyl methane, bisphenolic compounds like 2,2-methylene bis (4-chlorophenol), 2,2-methylene bis (3,4,6-trichlorophenol), 2,2-methylene bis (4-chloro-6-bromophenol), bis (2-hydroxy-3,5-dichlorophenyl) sulphide, and bis (2-hydroxy-5-chlorobenzyl)sulphide, benzoic esters (parabens) like methylparaben, propylparaben, butylparaben, ethylparaben, isopropylparaben, isobutylparaben, benzylparaben, sodium methylparaben, and sodium propylparaben, halogenated carbanilides (e.g., 3,4,4-trichlorocarbanilides (Triclocarban or TCC), 3-trifluoromethyl-4,4-dichlorocarbanilide, 3,3,4-trichlorocarbanilide, etc.).

Of these, preferred are phenol based non-cationic microbicidals (antimicrobial constituents), especially those based on one or more phenolic compounds, particularly 2-hydroxydiphenyl compounds which may be exemplified by the following classes of compounds:

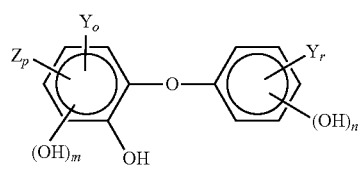

wherein Y is chlorine or bromine, Z is $SO_2$ H, $NO_2$, or $C_1$-$C_4$ alkyl, r is 0 to 3, o is 0 to 3, p is 0 or 1, m is 0 or 1, and n is 0 or 1. In preferred embodiments, Y is chlorine or bromine, m is 0, n is 0 or 1, o is 1 or 2, r is 1 or 2, and p is 0, and according to especially preferred embodiments, Y is chlorine, m is 0, n is 0, o is 1, r is 2, and p is 0.

Particularly useful 2-hydroxydiphenyl compounds include those which may be represented by the structure:

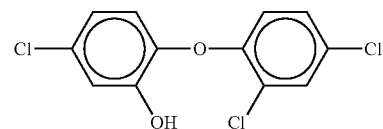

which is commonly referred to as "TRICLOSAN" and which is presently commercially available from Ciba Specialty Chemicals Corp., as well as halogenated carbanilides, e.g., TCC.

Further exemplary useful phenolic based antimicrobial constituents agents include 2,2'-hydroxy-5,5'-dibromo-diphenyl ether which may be represented by the structure:

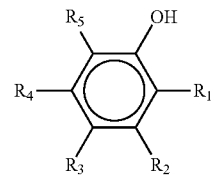

wherein $R_1$ is hydro, hydroxy, $C_1$-$C_4$ alkyl, chloro, nitro, phenyl, or benzyl; $R_2$ is hydro, hydroxy, $C_1$-$C_6$ alkyl, or halo; $R_3$ is hydro, $C_1$-$C_6$ alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid.

Still further useful phenol derivatives include those which may be represented by the structure:

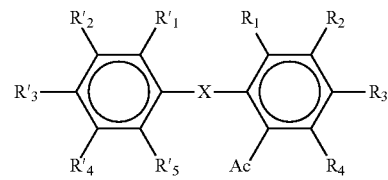

wherein X is sulfur or a methylene group, $R_1$ and $R'_1$ are hydroxy, and $R_2$, $R'_2$, $R_3$, $R'_3$, $R_4$, $R'_4$, $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Of the foregoing, a particularly useful phenol derivative is commonly referred to as triclocarban, or 3,4,4'-trichlorocarbanilide as well as derivatives thereto. When present, one or more such further compounds, constituents or materials which provide an effective microbicidal benefit.

A further and particularly referred antimicrobial constituent is salicylic acid and/or salicylic acid derivatives and/or a salt form thereof. Salicylates include octyl, amyl, phenyl, benzyl, menthyl, glyceryl, and dipropyleneglycol esters thereof). Specific examples of salicylic acid derivatives include: esters thereof including methyl salicylate, ethyl salicylate, butyl salicylate, propyl salicylate, isopropyl salicylate, 2,4-dinitrobenzyl salicylate, tolyl salicylates, naphthyl salicylates, trisalicylin furfuryl salicylate, and cyclohexyl salicylate; ethers thereof, including methoxy salicylic acid, ethoxy salicylic acid, propoxy salicylic acid, benzoxy salicylic acid, phenoxy salicylic acid, isopropoxy salicylic acid, p-ethylphenoxy-salicylic acid, and 2,4-dichlorophenoxy salicylic acid; acyl derivatives thereof including acetyl salicylic acid, salicyl salicylic acid, phenacyl salicylic acid, benzoyl salicylic acid, and p-nitrobenzoyl salicylic acid; as well as further salicylic acid derivatives including methylacetyl salicylate, ethyl salicylate, phenyl salicylate, benzyl salicylate. Salts of one or more of the foregoing may also be used, including inorganic and organic salts, and preferably the salt form of the salicylic acid and/or salicylic acid derivatives is water soluble or water miscible.

Advantageously salicylic acid and/or salicylic acid derivatives and/or a salt form thereof is present in a sufficient amount such that the compositions are effective against both gram positive and gram negative microorganisms.

A yet further and particularly referred antimicrobial constituent is lactic acid and/or lactic acid derivatives and/or salt forms thereof. Such include: lactic acid, salts thereof such as metal salts (e.g., sodium) as well as alkyl lactates such as the reaction products of a $C_8$-$C_{20}$ fatty alcohol with lactic acid. Preferred alkyl lactates include those represented by the following general structural formula (Ia):

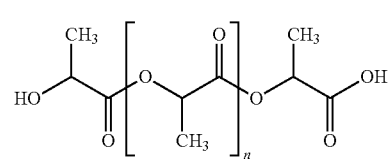

in which R is a $C_8$-$C_{20}$ alkyl moiety, preferably is a $C_{10}$-$C_{14}$ alkyl moiety and especially preferably is predominantly (at least 85%, more preferably at least 90%, particularly preferably at least 95% and most preferably at least about 98%) of a $C_{12}$ alkyl moiety. The alkyl moiety may be branched but is preferably substantially linear. Further preferred alkyl lactates also include those which may be represented by the following general structural formula (Ib):

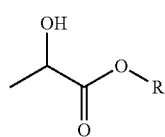

in which R is a $C_8$-$C_{18}$ alkyl moiety, preferably is a $C_{10}$-$C_{14}$ alkyl moiety and especially preferably is predominantly (at least 85%, more preferably at least 90%, particularly preferably at least 95% and most preferably at least about 98%) of a $C_{12}$ alkyl moiety. The alkyl moiety may be branched but is preferably substantially linear. Also useful are lactides as may be represented by the following formula (Ic):

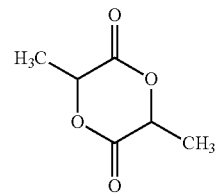

as well as polylactides as may be represented by the formula (Id):

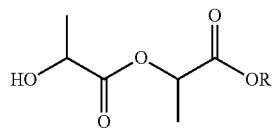

wherein n is an integer of at least 1, preferably n is an integer from 1-100 inclusive, and particularly preferably n is 1-3. Of course it is to be understood that other alkyl lactates not specifically encompassed by the compounds of formulae (Ia), (Ib), (Ic) and/or (Id) may also be utilized. The lactic acid and/or derivatives thereof may also be optionally substituted with one or more substituents, and by way of nonlimiting example, such substituents may be independently selected from alkyl, aryl, alcohol, ether, ester, cyanide, amide, amine, sulfate, phosphate, fluoro, chloro, bromo or iodo groups or carbonyl groups. The lactic acid, salt or derivative may also be provided deposited upon an inorganic carrier such as silica. Salts of one or more of the foregoing may also be used, including inorganic and organic salts, and preferably the salt form of the lactic acid and/or derivative is water soluble or water miscible.

Advantageously the lactic acid and/or lactic acid derivatives and/or a salt form thereof is present in a sufficient amount such that the compositions are effective against both gram positive and gram negative microorganisms.

The total amount of the antimicrobial constituent is preferably present in a microbicidally effective amount, such that the aqueous topical treatment compositions formed from the pulvurent effervescent topical treatment compositions are microbicidally effective against one or more undesired microorganisms, such as gram positive and/or gram negative bacteria. Such microorgansims include, inter alia, *E. coli*, *S. aureus*, *P. aeruginosa*, and *E. hirae*.

The pulvurent effervescent topical treatment compositions also include 0.0001-3% wt. of an exogenous product of *Sclerotium rolfsii*, which product (interchangeably referred to as "*Sclerotium* Gum") is described by its supplier (Alban Muller International; Paris, FR) as a homopolysaccharide containing glucose as its only monomer, and wherein the homopolysaccharide has a molecualar weight of 5,000,000-6,000,000 Daltons. This homopolysaccharide is believed to be represented as having the following monomer unit:

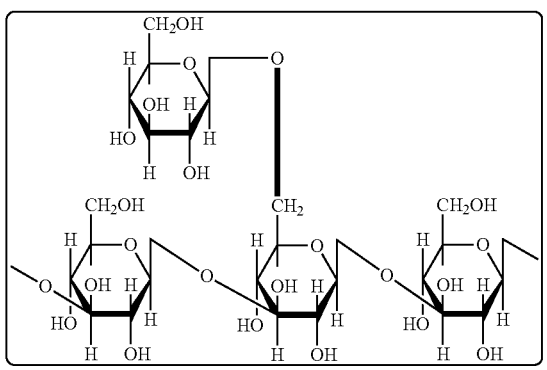

As is seen therefrom, the main chain of the homopolysaccharide includes glucose molecules linked by beta 1-3 links, and every third D-glucose molecule includes a further D-glucose molecule joined by a beta 1-6 link. While this material is at a known for use as a thickener and suspending agent in liquid compositions, e.g., lotions, gels, emulsions, its use in a pulvurent treatment compositions is believed to be novel. Moreso, prior to the present invention described herein, pulvurent effervescent topical treatment compositions comprising *Sclerotium* Gum is believed to be novel.

Preferably the pulvurent effervescent topical treatment compositions include 0.5-1.5% wt., more preferably between about 0.65-1.25% of an exogenous product of *Sclerotium rolfsii*, The pulvurent effervescent topical treatment compositions may optionally comprise one or more further constituents which impart a desired aesthetic benefit, and/or a desired technical benefit to the pulvurent effervescent topical treatment compositions and/or to the aqueous topical treatment compositions formed from the pulvurent effervescent topical treatment compositions. Generally the cumulative amount of these one or more further optional constituents do not exceed 20% wt., preferably do not exceed 15% wt., and particularly preferably do not exceed 10% wt. of the pulvurent effervescent topical treatment compositions of which they form a part.

Non-limiting examples of optional constituents which impart aesthetic benefits include fragrances, perfumes, colorants, optical brighteners.

Non-limiting examples of optional constituents which impart a technical benefit include organic solvents and in particular carrier constituents provided as part of fragrance preparations and concentrates, hydrotropes, inert particulate materials such as abrasives, fillers and bulking agents, pH adjusting agents, pH buffers and chelating agents.

Exemplary useful chelating agents include those known to the art, including by way of non-limiting example; aminopolycarboxylic acids and salts thereof wherein the amino nitrogen has attached thereto two or more substituent groups, alkali metal, ammonium and substituted ammonium polyacetates, carboxylates, polycarboxylates and polyhydroxysulfonates, as well as tetra sodium salt of glutamic acid-N,N-diacetic acid, as well as methyl-glycine-diacetic acid. Preferred chelating agents include acids and salts, especially the sodium and potassium salts of ethylenediaminetetraacetic acid, diethylenetriaminepentaacetic acid, N-hydroxyethylethylenediaminetriacetic acid, and of which the sodium salts of ethylenediaminetetraacetic acid may be particularly advantageously used. Nonlimiting examples of commercially available chelating agents include those marketed under the "Dissolvine" trademark (ex. AkzoNobel) including Dissolvine GL-PD-S, and Dissolvine E-CA-10 materials. The inclusion of a chelating agent is a preferred embodiment of the invention, in that the inclusion of the chelating agent in the pulvurent effervescent topical treatment compositions chelates undesired ions which may be present in the water which is combined with the pulvurent effervescent topical treatment compositions and used to form the aqueous topical treatment compositions.

The pulvurent effervescent topical treatment compositions may optionally comprise one or more filler constituents, preferably based on materials which inert with respect to the gas generating constituent and which also are inert with respect to the antimicrobial constituent. Such are provided as comminuted or particulate materials. These inert filler materials may be compounds or materials which are preferably insoluble in water and/or in organic solvents. Non-limiting examples of such include silicates such as sodium silicate and aluminum silicate, chemically modified magnesium aluminum silicate, hydrated aluminum silicate, fumed silica, silica dioxide, talc (layered magnesium silicate), alkali metasilicates, e.g., sodium metasilicate and the like, perlite, pumice, feldspar, calcium phosphate, chalk, kaolin, carbon black, insoluble sulfates such as sodium sulfate, and mixtures thereof.

The pulvurent effervescent topical treatment compositions may be produced by simple mixing of measured amounts of the individual constituents which are preferably also supplied in the form of a granulated, or pulvurent forms, and mixed such as by blending, tumbling or any other technique which provides a homogeneous blend of the constituents.

The pulvurent effervescent topical treatment compositions may be packaged into any suitable container, and dispensed therefrom as required. Non-limiting examples of such dispensers include bulk dispensers such as bottles, jars, and bags. Further dispensers may be unit dose dispensers wherein a measured quantity of a pulvurent effervescent topical treatment composition is provided at amount which is appropriate for addition to a unit amount of water, e.g, 1 liter, e.g., a 100 gram amount of the pulvurent effervescent topical treatment compositions for use in a 900-1000 ml aliquot of water.

Further dispensers, e.g., unit dose dispensers, are in the form of water dispersible, water miscible or water soluble sachet or pouch or water-soluble package containing the pulvurent effervescent topical treatment compositions. Such may be formed from a water soluble material, such as a water soluble or water dispersible polymeric film (e.g. polyvinyl alcohol), or alternately may be formed from a water insoluble material, such as a water insoluble polymeric film. Such may be flexible films, or may be rigid films or bodies formed from such water soluble materials. Additionally the sachet, pouch or package may be formed in a manner where only part of the sachet is physically breachable or only part of the sachet, pouch or package is water soluble or dispersible which encases a quantity of the pulvurent effervescent topical treatment compositions. When such a unit dose dispenser is added to a unit quantity of water, the water soluble polymer dissolves and releases the pulvurent effervescent topical treatment compositions to the water which is dissolved or dispersed within and thereby forming a the aqueous topical treatment compositions which is effervescent and forms foam. Thus a further aspect of the invention provides a closed, a water dispersible, a water miscible or a water soluble sachet or pouch containing the inventive composition as described herein.

In a further embodiment the unit dose dispensers may be rigid capsules formed of water soluble materials, e.g., gelatine capsules or other preformed rigid encapsulating containers which are breachable, or soluble, in water.

In a still further embodiment the pulvurent effervescent topical treatment compositions may be tabletted into a shaped body, such as a pill, tablet or other three-dimensional body having an outer surface surrounding an interior volume. Preferably such a tabletted shaped body is frangible wherein it may be divided, or crushed prior to addition to a volume of water. Such tabletted shaped bodies may be provided in a carrier or tray, or may be individually provided such as in an overwrap of a material, preferably a water impermeable material, and/or the outer surface may be coated with a water soluble polymer or other water soluble material which provides a tablet coating which limits the transmission of ambient air humidity to the interior volume.

The generation of the gas by the gas generating constituent also aids in the mixing of the constituents of the pulvurent effervescent topical treatment composition in the water, frequently without requiring any manual stirring by a user of the product.

In a further embodiment, the pulvurent effervescent topical treatment compositions may be may be provided with a carrier substrate. One example of a useful carrier substrate is a wipe. The wipe can be of a woven or non-woven nature. Such include fabric substrates which can include nonwoven or woven pouches, sponges including both closed cell and open celled sponges, e.g., sponges formed from celluloses as well as other polymeric materials, as well as in the form of abrasive or non-abrasive cleaning pads. Such fabrics are known commercially in this field and are often referred to as wipes. Such substrates can be resin bonded, hydroentangled, thermally bonded, meltblown, needlepunched, or any combination of the former. The carrier substrate useful with the present inventive compositions may also be a wipe which includes a film forming substrate such as a water soluble polymer. Such self-supporting film substrates may be sandwiched between layers of fabric substrates and heat sealed to form a useful substrate.

The pulvurent effervescent topical treatment compositions of the present invention are advantageously absorbed onto the carrier substrate, i.e., a wipe to form a ready to use wipe article. The wipe can then be sealed individually in a pouch which can then be opened when needed or a multitude of wipes can be placed in a container for use on an as needed basis. The container, when closed, sufficiently sealed to prevent ingress of water prior to use in treating a topical surface. In use, a wipe is removed from the container, then placed in contact with sufficient water in order to cause effervescing of the pulvurent effervescent topical treatment at which time, or after which time, the wipe article (or other carrier substrate) is contacted with a topical surface. In such a product format the provision of a wipe or other carrier substrate is particularly convenient for use by a consumer as the wipe or other carrier substrate functions to deliver the effervescing, foamed topical treatment composition (viz. the aqueous topical treatment compositions) directly upon the topical surface, and to also wipe the topical surface after it has been treated.

In a preferred embodiment and method of application, a quantity of essentially anhydrous pulvurent effervescent topical treatment compositions is supplied to a topical surface, e.g., hands, face, part of the body, and thereafter water is applied to the pulvurent effervescent topical treatment compositions which very rapidly forms an effervescing, foamed topical treatment composition (viz. the aqueous topical treatment compositions) directly upon the topical surface.

In a preferred embodiment and method of application, a quantity of essentially anhydrous pulvurent effervescent topical treatment compositions is supplied to an aliquot of water, e.g., a quantity of water in a vessel or container (e.g., pail, dish,) and thereafter the formed effervescing, foamed topical treatment composition (viz. the aqueous topical treatment composition) may be applied to topical surfaces, e.g., hands, face, part of the body. In such an embodiment, the effervescing, foamed topical treatment composition are used as bodywash compositions, topical rinse compositions, and the like.

When topically applied the aqueous topical treatment compositions provide a cleaning benefit an concurrently an antimicrobial benefit to the contacted topical surfaces. Optionally after providing such benefits, the applied aqueous topical treatment compositions may be rinsed of with a further quantity of water and/or wiped off the topical surface.

Certain embodiments of the invention, including certain particularly preferred embodiments of the invention are disclosed in the following examples.

EXAMPLES

A number of pulvurent effervescent topical treatment compositions were produced by mixing the constituents, each of which was in a comminuted, powered or particulate form, as outlined in Table 1 by adding measured amounts of the individual constituents into an open mouthed vessel, and thereafter manually mixing the constituents until a homogenous mixture resulted. Typically mixing required 5-10 minutes. In the following Table 1, the amounts listed are % wt. of the indicated constituent.

TABLE 1

|  | E1 | E2 | E3 | E4 | E5 | E6 | E7 |
|---|---|---|---|---|---|---|---|
| cocosulfate | 20.0 | 20.0 | 20.0 | 20.0 | 15.0 | 14.0 | 14.0 |
| sodium bicarbonate | 60.0 (0.714 mol) | 73.2 (0.871 mol) | 71.25 (0.848 mol) | 59.05 (0.702 mol) | 53.0 (0.631 mol) | 49.0 (0.583 mol) | 49.95 (0.595 mol) |
| citric acid | 5.0 (0.026 mol) | 5.0 (0.026 mol) | 3.0 (0.015 mol) | 15.0 (0.078 mol) | 30 (0.156 mol) | 35.0 (0.182 mol) | 35.0 (0.182 mol) |
| salicylic acid | 0.3 | 0.3 | 0.3 | 0.3 | 0.3 | 0.3 | — |
| lactic acid (60%) | — | — | — | — | — | — | 3.35 |
| dissolvine | 0.2 | 0.2 | 0.2 | 0.2 | 0.4 | 0.4 | 0.4 |
| "Sclerotium Gum" | 0.2 | 1.0 | 1.0 | 1.0 | 1.0 | 1.0 | 1.0 |
| silica | — | — | 4.0 | 4.0 | — | — | — |

TABLE 1-continued

|  | E1 | E2 | E3 | E4 | E5 | E6 | E7 |
|---|---|---|---|---|---|---|---|
| sodium sulfate | — | — | 0.15 | 0.15 | — | — | — |
| talc | 14.0 | — | — | — | — | — | — |
| fragrance | 0.3 | 0.3 | 0.1 | 0.3 | 0.3 | 0.3 | 0.3 |

The identity of the specific constituents are identified on the following Table 2, and were used 'as supplied" from their supplier or source. In addition to the identity of the constituent, the % wt. active and in some instances the source of the constituent is also indicated.

TABLE 2

| cocosulfate | sodium cocosulfate,, Mackol ® CAS-100N, 90-100% wt. active (ex. Rhodia). |
|---|---|
| sodium bicarbonate | laboratory grade anhydrous $NaHCO_3$, 100% wt. active, |
| citric acid | laboratory grade anhydrous citric acid, 100% wt. active, |
| salicylic acid | laboratory grade anhydrous salicylic acid, 100% wt. active, (ex. Sigma or Aldrich) |
| lactic acid (60%) | anhydrous lactic acid on calcium lactate carrier, Purac ® Powder 60, 60% wt. active acid concentration (ex. Corbion Caravan) |
| dissolvine | chelating agent, Dissolvine GL-47-S, tetrasodium glutamate diacetate 100% wt. active (ex. AkzoNobel) |
| "Sclerotium Gum" | exogenous product of Sclerotium rolfsii, 100% wt. active (Amigel ®, ex. Alban Muller International; Paris, FR) |
| silica | anhydrous silica powder, 100% wt. active |
| sodium sulfate | anhydrous sodium sulfate, 100% wt. active |
| talc | anhydrous sodium sulfate, 100% wt. active |
| fragrance | proprietary composition of its supplier, used as 100% wt. active |

Each of the example compositions were essentially dry, free flowing powders which when added to a quantity of water, at a 10% w/w concentration, rapidly effervesced and foamed.

Antimicrobial Testing:

Compositions E5, E6 and E7 were evaluated for antimicrobial efficacy against two challenge organisms. The compositions were tested according to the following protocol:

Compositions according to E5, E6 and E7 of Table 1 were produced and used for antimicrobial testing, and stored at room temperature prior to testing.

For testing, a suitable neutralizer was prepared, by combining 100 g. Tween 80, 30 g lecithin, 5 g sodium thiosulfate, 1 g L-histidine, 10 ml of phosphate buffer to 900 ml of distilled water.

For testing Tryptic Soy agar, was combined with 7 g/liter of lecithin, and 5 g/liter of Tween 80 and used to culture the challenge organisms after testing.

For testing, a standardized water sample was prepared by adding $CaCO_3$ to distilled water to a final concentration of 300 mg/liter. (Known as 'hard water'.)

The challenge organisms were Staphylococcus aureus (ATCC 6538) and Escherichia coli (ATCC 10536). The microorganisms were a second or third generation subculture on TSA slopes from frozen beads. Subcultures are prepared on TSA slopes ("slants") and incubated at 35±2.5° C. for 18-24 hours. Test cultures were prepared by removing at least two loopfulls of the appropriate TSA slants and the cells were suspended in approximately 10 mL of TSC, and rotated at a rate of 150 rotations/minute for at least three minutes. Thereafter, a portion of the suspended cells was pipetted, and added to an appropriate volume of TSC and the concentrations of the challenge organisms were adjusted to provide $1.5-5 \times 10^8$ cfu/ml for each organism. The concentrations were adjusted according to a known method, e.g. measured utilizing the biolog transmittance; the typical transmittance range of between about 30 and about 50 (biolog) was used for each of the S. aureus (ATCC 6538) and E. coli (ATCC 10536) challenge microorganisms.

Testing of the test substances was performed according to one of the following Test methods.

Test 1: 5.55% m/v dilutions of each of the samples tested were prepared using test temperature (37° C.) calibrated hard water to give an in-test dilution of 5%. 9.0 mL aliquots of the diluted test sample were then transferred to sterile tubes for testing. Within 1.5 to 2 minutes after preparation of the test dilution, 1.0 mL of the challenge microorganism (equilibrated to the test temperature) was added to the tube, vortexed and placed back in the temperature controlled waterbath for the duration of the contact time. Two replicates of each of the diluted samples were tested.

Test 2: 0.56 g of product was added to a sterile test tube, 9.0 mL of test temperature (37° C.) calibrated hard water was added and immediately (within 10 to 20 seconds), 1.0 mL of the challenge microorganism (equilibrated to the test temperature) was added to the tube, vortexed and placed back in the temperature controlled waterbath for the duration of the contact time. (To give an in-test dilution of 5%.) One replicate of each of the diluted samples was tested.

Note: Upon addition of the standardized water sample to each test tube, during both sets of testing, samples of E5, E6 or E7 were observed to foam spontaneously within the test tube.

For both tests, the contact time time was 60±5 seconds contact times whereas samples were subsequently neutralized for 5 minutes and then appropriate dilutions were prepared and then pour plated using the agar previously described. The agar test plates were then incubate at 35-5–36-5° C. for 48 hours, and then evaluated for the $\log_{10}$ reduction of the initial challenge organisms present. These results are reported on Table 3, following.

The results of the test are reported on Table 3.

TABLE 3

|  | Test 1 S. aureus (ATCC 6538) $\log_{10}$ reduction | Test 1 E. coli (ATCC 10536) $\log_{10}$ reduction | Test 2 S. aureus (ATCC 6538) $\log_{10}$ reduction | Test 2 E. coli (ATCC 10536) $\log_{10}$ reduction |
|---|---|---|---|---|
| E5 | 1.10 0.99 | 0.75 0.04 | >5.38 | 0.05 |
| E6 | 1.03 1.74 | 0.06 <0.07 | >5.38 | No Reduction |
| E7 | 1.76 1.64 | 0.09 0.13 | >5.38 | 0.12 |

As can be seen from the foregoing table, the compositions were particularly effective against S. aureus, a gram positive type microorganism, with lesser but still effective results against E. coli, a gram negative type microorganism.

The invention claimed is:

1. A pulvurent effervescent topical treatment composition which comprises:
   at least 50% wt. of a gas generating system which comprises both a gas generating constituent as well as a complementary reactive acid constituent, which constituents, when combined in the presence of water or another largely aqueous medium generates carbon dioxide;
   5-50% wt. of an anionic soap and/or anionic surfactant constituent;
   0.0001-1.5% wt. of an antimicrobial constituent;
   0.0001-3 an exogenous product of *Sclerotium rolfsii*,
   a chelating agent,
   characterized in that the composition excludes inert particulate materials.

2. A composition according to claim 1 wherein the antimicrobial constituent is selected from: salicylic acid and/or salicylic acid derivatives and/or a salt form thereof.

3. A composition according to claim 1 wherein the antimicrobial constituent is selected from: lactic acid and/or lactic acid derivatives and/or a salt form thereof.

4. A composition according to claim 3 wherein the antimicrobial constituent is an alkyl lactate.

5. A composition according to claim 1 wherein which comprises a cocosulfate anionic surfactant.

6. A composition according to claim 1, wherein the said composition is effective against one or more of the following microorganisms: *E. coli, S. aureus, P. aeruginosa*, and *E. hirae*.

7. A composition according to claim 1, wherein the chelating agent is selected from the group consisting of: aminopolycarboxylic acids and salts thereof wherein the amino nitrogen has attached thereto two or more substituent groups, alkali metal, ammonium and substituted ammonium polyacetates, carboxylates, polycarboxylates and polyhydroxysulfonates, tetra sodium salt of glutamic acid-N,N-diacetic acid, methyl-glycine-diacetic acid, sodium and potassium salts of ethylenediaminetetraacetic acid, diethylenetriaminepentaacetic acid, N-hydroxyethylethylenediaminetriacetic acid.

8. A composition according to claim 1 in the form of a tableted body.

9. A composition according to claim 1, wherein the composition is absorbed onto a carrier substrate and forms a wipe article.

10. A method for providing an antimicrobial benefit to an epidermal surface which method includes the step of:
    applying an antimicrobially effective amount of a topical germicidal composition according to claim 1.

11. A pulvurent effervescent topical treatment composition consisting of:
    at least 50% wt. of a gas generating system which comprises both a gas generating constituent as well as a complementary reactive acid constituent, which constituents, when combined in the presence of water or another largely aqueous medium generates carbon dioxide;
    5-50% wt. of an anionic soap and/or anionic surfactant constituent;
    0.0001-1.5% wt. of an antimicrobial constituent;
    0.0001-3 an exogenous product of *Sclerotium rolfsii*,
    optionally, one or more further constituents selected from organic solvents, fragrances, perfumes, colorants and optical brighteners, nonionic surfactants, cationic surfactants, hydrotropes, chelating agents, pH buffers and pH adjusting agents.

12. A composition according to claim 11 wherein the antimicrobial constituent is selected from: salicylic acid and/or salicylic acid derivatives and/or a salt form thereof.

13. A composition according to claim 11 wherein the antimicrobial constituent is selected from: lactic acid and/or lactic acid derivatives and/or a salt form thereof.

14. A composition according to claim 13 wherein the antimicrobial constituent is an alkyl lactate.

15. A composition according to claim 11 wherein which comprises a cocosulfate anionic surfactant.

16. A composition according to claim 11, wherein the said composition is effective against one or more of the following microorganisms: *E. coli, S. aureus, P. aeruginosa*, and *E. hirae*.

17. A method for providing an antimicrobial benefit to an epidermal surface which includes the step of:
    applying an antimicrobially effective amount of a composition according to claim 11 to thereby reduce the incidence of undesired microorganisms present on the treated epidermal surface.

* * * * *